United States Patent
Nakamura

(10) Patent No.: US 12,260,369 B2
(45) Date of Patent: Mar. 25, 2025

(54) SYSTEM FOR DETERMINING WHETHER USER IS ACTUALLY IN POSSESSION OF ELECTRONIC DEVICE PROVIDING LOCATION INFORMATION, AND STORAGE MEDIUM AND DETERMINATION METHOD FOR SAME

(71) Applicant: CASIO COMPUTER CO., LTD., Tokyo (JP)

(72) Inventor: Fuminobu Nakamura, Tokyo (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 0 days.

(21) Appl. No.: 18/229,223

(22) Filed: Aug. 2, 2023

(65) Prior Publication Data
US 2023/0376886 A1 Nov. 23, 2023

Related U.S. Application Data

(63) Continuation of application No. PCT/JP2022/000299, filed on Jan. 7, 2022.

(30) Foreign Application Priority Data

Feb. 19, 2021 (JP) .................. 2021-025367

(51) Int. Cl.
*G06Q 10/0836* (2023.01)
*H04L 9/40* (2022.01)
*H04W 12/69* (2021.01)

(52) U.S. Cl.
CPC ..... *G06Q 10/0836* (2013.01); *H04L 63/0861* (2013.01); *H04W 12/69* (2021.01)

(58) Field of Classification Search
CPC ............. G06Q 10/0834; G06Q 10/08
See application file for complete search history.

(56) References Cited

U.S. PATENT DOCUMENTS 10,701,067 B1 * 6/2020 Ziraknejad ............ H04W 12/63
2011/0307282 A1 * 12/2011 Camp .................... G06Q 10/02
705/30

(Continued)

FOREIGN PATENT DOCUMENTS

JP 2008073462 A 4/2008
JP 2017033393 A 2/2017

(Continued)

OTHER PUBLICATIONS

DoorDashRash; "Great! They put an end to GPS spoofing"; Nov. 11, 2019; https://www.reddit.com/r/doordash/comments/duwx6f/great_they_put_an_end_to_gps_spoofing/ (Year: 2019).*

(Continued)

*Primary Examiner* — Rupangini Singh
*Assistant Examiner* — David G. Godbold
(74) *Attorney, Agent, or Firm* — Holtz, Holtz & Volek PC

(57) ABSTRACT

The purpose of the present invention is to provide a system, a storage medium, and a determination method capable of appropriately determining whether or not a delivery person is near a store where the delivery person receives a product. A delivery system includes: a delivery person terminal and a delivery management server, the delivery person terminal includes: a communication circuit which communicates with a delivery management server; one or more processors performs the following: acquiring first position information indicating the current position of the delivery person terminal; acquiring biometric information on a delivery person (user) or body movement information; and acquiring possession state information indicating whether the delivery person terminal is possessed by the user, based on the acquired biometric information or the acquired body movement information, controlling the communication circuit to transmit, to the delivery management server, the first posi- (Continued)

tion information and the possession state information regarding the possession state of the user determined.

9 Claims, 12 Drawing Sheets

(56) References Cited

U.S. PATENT DOCUMENTS

| | | | | |
|---|---|---|---|---|
| 2016/0300185 | A1* | 10/2016 | Zamer | G06Q 10/08355 |
| 2019/0104391 | A1 | 4/2019 | Tajima | |
| 2019/0164126 | A1* | 5/2019 | Chopra | G06Q 10/0834 |
| 2021/0082271 | A1* | 3/2021 | Mars | H04W 4/80 |
| 2021/0365865 | A1* | 11/2021 | Jones | H04W 72/0453 |
| 2022/0180310 | A1* | 6/2022 | Leoni | G06Q 10/0834 |

FOREIGN PATENT DOCUMENTS

| | | |
|---|---|---|
| JP | 2020017050 A | 1/2020 |
| WO | 2017208363 A1 | 12/2017 |

OTHER PUBLICATIONS

International Search Report (ISR) (and an English language translation thereof) dated Mar. 8, 2022, issued in International Application No. PCT/JP2022/000299.

Written Opinion dated Mar. 8, 2022, issued in International Application No. PCT/JP2022/000299.

Japanese Office Action (and an English language translation thereof) dated Oct. 1, 2024, issued in counterpart Japanese Application No. 2021-025367.

Japanese Office Action (and an English language translation thereof) dated Oct. 10, 2024, issued in counterpart Japanese Application No. 2021-025367.

* cited by examiner

SYSTEM FOR DETERMINING WHETHER USER IS ACTUALLY IN POSSESSION OF ELECTRONIC DEVICE PROVIDING LOCATION INFORMATION, AND STORAGE MEDIUM AND DETERMINATION METHOD FOR SAME

TECHNICAL FIELD

The present invention relates to a system, a storage medium, and a determination method.

BACKGROUND ART

In conventionally known systems, the server acquires the location information of potential deliverers, and selects a deliverer who is near the store where the product will be received. Since the location information is sent from an electronic device such as a smartphone held by a deliverer, a deliverer near the store where the product will be received is preferentially selected, reducing delivery time. Patent Document 1 discloses this type of technology.

Patent Document 1 pertains to an information processing device that provides a system to allow general users to be product deliverers. Patent Document 1 discloses an information processing device that acquires contact information paired with candidate location information having a predetermined relationship with store location information paired with a product identifier included in a delivery request received from a deliverer terminal, and sends offer information to the candidate.

Patent Document 1: Japanese Unexamined Patent Application, Publication No. 2020-17050

DISCLOSURE OF THE INVENTION

However, when a deliverer is selected based on the location information of the electronic device possessed by the deliverer, if the electronic device is fixed near the store where the product will be received, the deliverer who possesses the electronic device will be preferentially selected. A malicious deliverer could use a relay terminal and receive orders even if the deliverer is not near the store, causing delivery delays.

An aspect of the present disclosure provides a system includes: an electronic device and a server, the electronic device, comprises: a first wireless communication circuit that communicates with the server; and one or more processors that performs the following: acquiring first location information indicating a current location of the electronic device; acquiring biometric information or body motion information of a user; and acquiring possession status information indicating whether the electronic device is possessed by the user, based on the acquired biometric information or the acquired body motion information, controlling the first wireless communication circuit to send the possession status information along with the first location information to the server, and the server, comprising: a communication circuit that communicates with the electronic device; and one or more processors that performs the following: acquiring the possession status information and the first location information from the electronic device; determining whether a delivery order is to be placed, based on the acquired first location information and the acquired possession status information.

PREFERRED MODE FOR CARRYING OUT THE INVENTION

Hereinafter, an embodiment of the present invention will be described with reference to the drawings.

<Delivery System>

Figure 1:
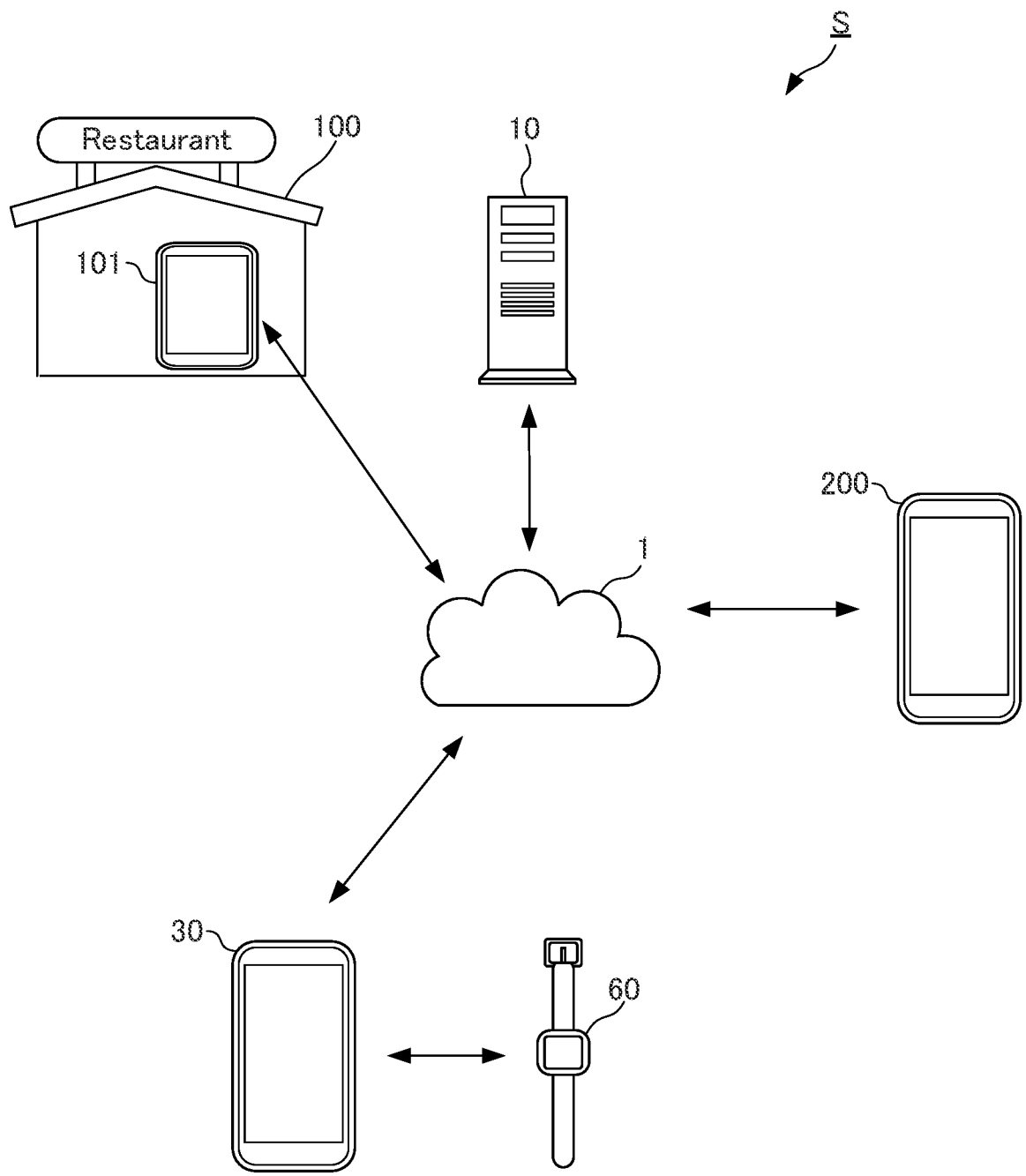
FIG. 1 is a schematic diagram of a delivery system, to which a delivery management server according to an embodiment of the present invention is applied.

An overview of a delivery system S is described. FIG. 1 is a schematic diagram of the delivery system S, in which a delivery management server 10 according to an embodiment of the present invention is applied. Note that the term "system" herein is intended to mean a comprehensive apparatus configured by a plurality of devices or a plurality of means, etc.

The delivery system S of the present embodiment is implemented by the delivery management server 10 that manages delivery. The delivery management server 10 receives delivery orders of products from a designated store 100 via a network 1 such as the Internet from an orderer terminal 200. The delivery management server 10 sends order information to a store-side terminal 101 installed in the store 100 via the network 1, while sending delivery-related information to a deliverer terminal 30. After the delivery processing, the delivery management server 10 sends information indicating the delivery status to the orderer terminal 200.

The delivery management server 10 may be a general-purpose computer that can execute various functions by installing various programs, or may be a computer built into dedicated hardware.

The deliverer terminal 30 is a first electronic device possessed by the deliverer. The deliverer terminal 30 is a portable computer such as a smartphone, tablet, etc. The wearable terminal 60 is a wearable electronic device such as a smartwatch, etc. The wearable terminal 60 pairs with the deliverer terminal 30 to send and receive various information.

The orderer terminal 200 is an electronic device possessed by the orderer. The orderer terminal 200 is a portable computer such as a smartphone, tablet, etc., or a stationary computer such as a desktop computer.

The store-side terminal 101 is a terminal installed in the store 100. The store-side terminal 101 is a portable computer such as a smartphone, tablet, etc., or a stationary computer such as a desktop computer.

<Delivery Management Server>

Figure 2:
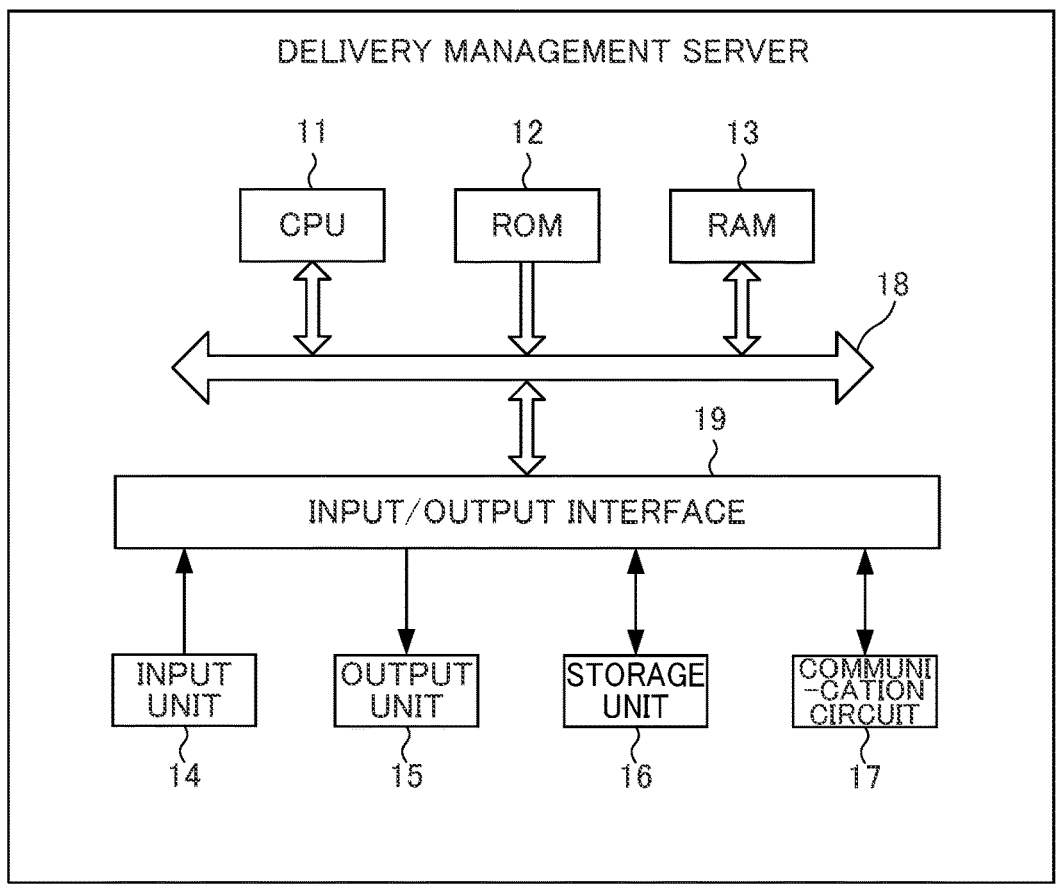
FIG. 2 is a block diagram illustrating a hardware configuration of the delivery management server according to an embodiment of the present invention.

Next, an example of the delivery management server 10 is described. FIG. 2 is a block diagram illustrating the hardware configuration of the delivery management server 10 according to an embodiment of the present invention.

The delivery management server 10 includes a CPU (Central Processing Unit) 11, a ROM (Read Only Memory) 12, a RAM (Random Access Memory) 13, an input unit 14, an output unit 15, a storage unit 16, and a communication circuit 17.

The CPU 11, ROM 12, and RAM 13 are interconnected via a bus 18. The CPU 11 executes various processing according to a program recorded in the ROM 12 or a program loaded in the RAM 13.

The bus 18 is also connected to an input/output interface 19. The input unit 14, the output unit 15, the storage unit 16, and the communication circuit 17 are connected to the input/output interface 19.

The input unit 14 and the output unit 15 are user interfaces electrically connected to the input/output interface 19, either by wired or wireless means. The input unit 14 is configured by elements such as a keyboard or mouse, while the output unit 15 is configured by devices such as a display for visual output and speakers for audio output. Note that the output unit 15 and input unit 14 can be integrated as a single unit, such as a touch panel.

The memory unit 16 is configured by semiconductor memory like DRAM (Dynamic Random Access Memory), and serves as a device for storing various data of the delivery management server 10.

The communication circuit 17 is a circuit for the CPU 11 to communicate with other computers via a network 1 such as the Internet.

Figure 3:
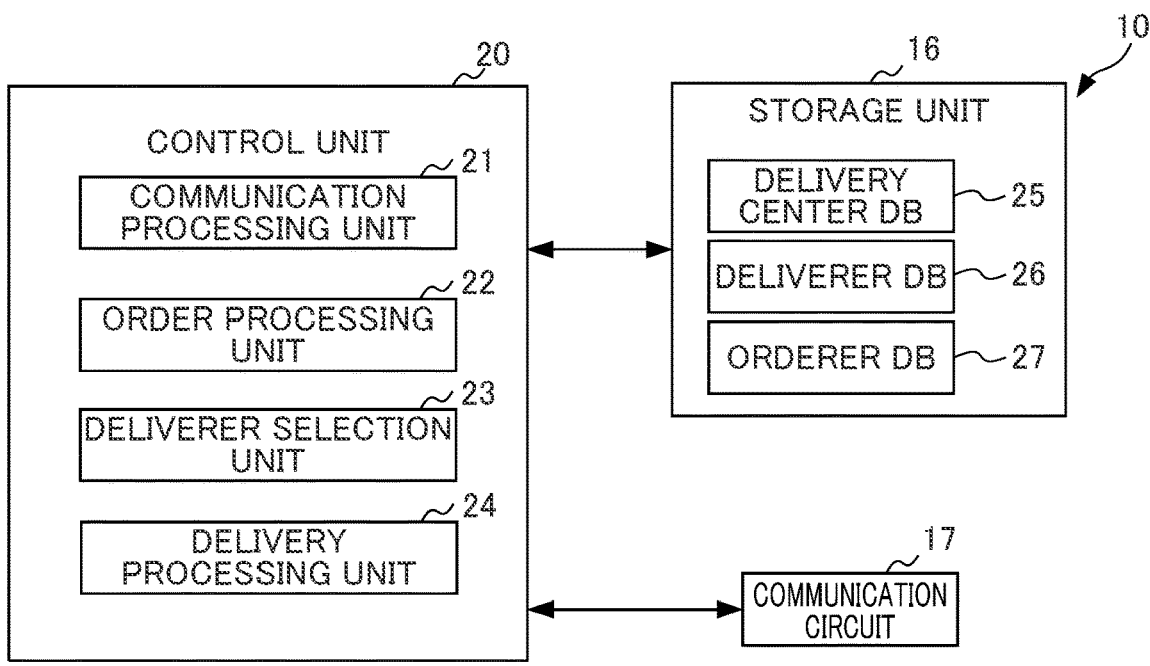
FIG. 3 is a functional block diagram illustrating a part of a functional configuration of the delivery management server according to an embodiment of the present invention.

Next, the functional configuration of the delivery management server 10 will be described. FIG. 3 is a functional block diagram illustrating the functional configuration for executing delivery management of the delivery management server 10 according to an embodiment of the present invention.

The control unit 20, which manages various controls of the delivery management server 10, is implemented by the CPU 11 that executes computation processing.

A delivery center database 25, a deliverer database 26, and an orderer database 27 are constructed in the memory unit 16. The delivery center database 25 stores information on the connection point of the store-side terminal 101 of the store 100 that is registered in advance, the location of the store 100, products, etc. The deliverer database 26 stores information on the deliverer terminal 30 that is possessed by a pre-registered deliverer, while the orderer database 27 stores information on the product specified by the orderer, the location information for receiving the product, payment information, etc.

The control unit 20 of the present embodiment performs as a communication processing unit (communication processing function) 21, an order processing unit (order processing function) 22, a deliverer selection unit (deliverer selection function) 23, and a delivery processing unit (delivery processing function) 24.

The CPU 11 as communication processing unit 21 executes processing for communication with external devices via the communication circuit 17. For example, the communication processing unit 21 executes processing for sending and receiving various types of information with the orderer terminal 200 and the deliverer terminal 30, which are connected to the delivery management server 10.

The CPU 11 as order processing unit 22 executes processing for receiving a delivery of products from the orderer terminal 200. For example, when the order processing unit 22 receives order information on the store 100 and the product specified by the orderer from the orderer terminal 200, the order processing unit 22 refers to the delivery center database 25, and sends the order information to the specified store-side terminal 101. The order processing unit 22 also executes processing related to a purchase of products.

The CPU 11 as deliverer selection unit 23 references the deliverer database 26 and the orderer database 27 constructed in the memory unit 16, and extracts a plurality of deliverer candidates. The deliverer selection unit 23 acquires location information of the plurality of deliverers and executes processing of selecting a deliverer, based on predetermined criteria. This processing of selecting a deliverer will be described later.

The CPU 11 as delivery processing unit 24 receives information on the delivery status from the deliverer terminal 30 of the deliverer selected by the deliverer selection unit 23, and executes processing of sending information on the delivery status to the orderer terminal 200.

<Deliverer Terminal>

Figure 4:
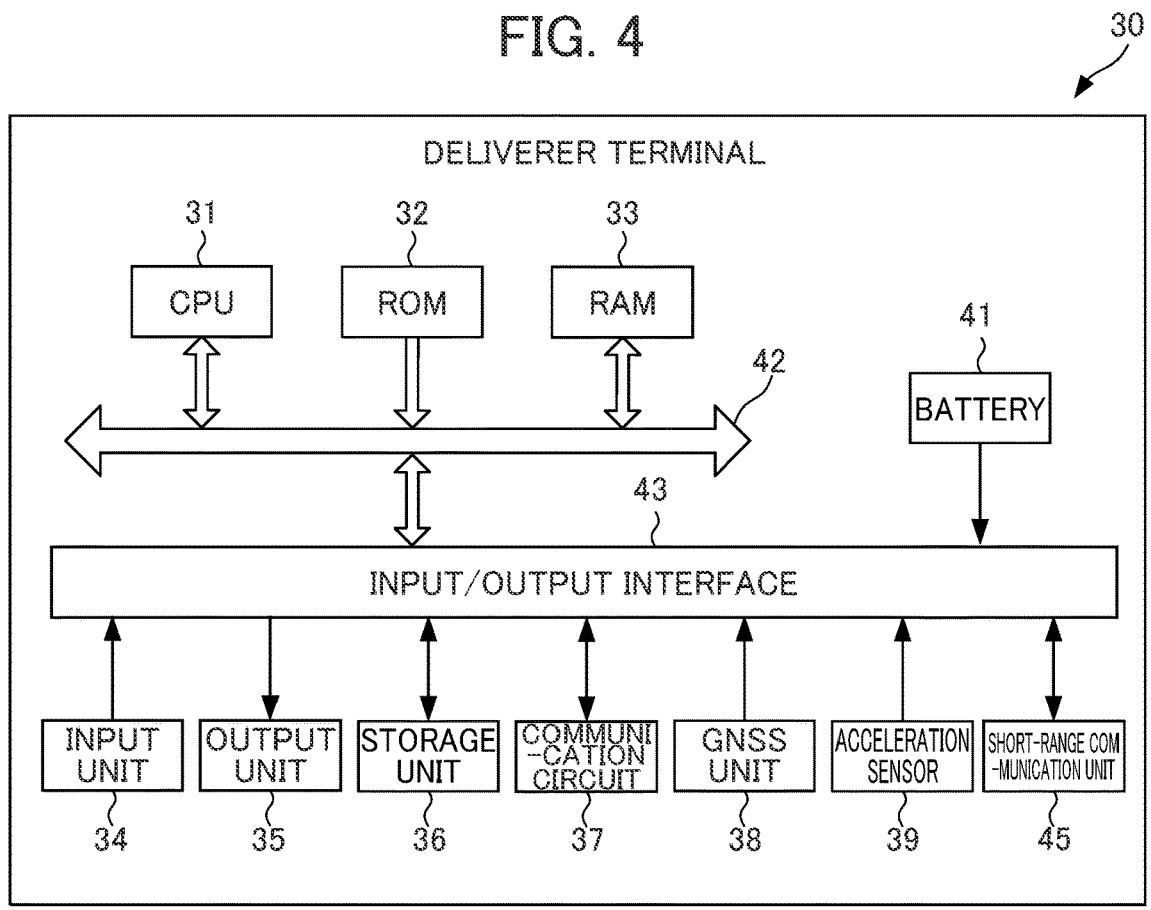
FIG. 4 is a block diagram illustrating the hardware configuration of the deliverer terminal according to an embodiment of the present invention.

Next, an example of the deliverer terminal 30 will be described. FIG. 4 is a block diagram illustrating the hardware configuration of the deliverer terminal 30 according to an embodiment of the present invention.

The deliverer terminal 30 in the present embodiment is a computer provided with a CPU 31, a ROM 32, a RAM 33, an input unit 34, an output unit 35, a memory unit 36, a communication unit 37, a GNSS unit 38, an acceleration sensor 39, a battery 41, a bus 42, an input/output interface 43, and a short-range communication unit 45. Note that the same names may be assigned to common or similar configurations already described, and the detailed description thereof may be omitted.

The communication circuit (first wireless communication circuit) 37 of the deliverer terminal 30 is a circuit for CPU 31 to communicate with the delivery management server 10 via a network 1 such as the Internet.

The GNSS unit 38 is a positioning information acquisition unit for acquiring location information. GNSS is an abbreviation for Global Navigation Satellite System, and the GNSS unit 38 uses a satellite positioning system such as GPS.

The GNSS Unit 38 includes an antenna, and is a circuit to perform positioning based on positioning satellite signals sent from a plurality of positioning satellites, and identifies its own position.

The acceleration sensor 39 is a device that detects movement and acceleration in arbitrary directions. For example, the acceleration sensor 39 is a three-axis sensor of a capacitive type or piezoresistive type, and detects acceleration occurring in each of the three axes.

The battery 41 supplies power to the deliverer terminal 30. For example, the battery 41 is configured by a lithium-ion battery.

The short-range communication unit 45 is a second wireless communication unit that communicates with the wearable terminal 60. The short-range communication unit 45 communicates with the wearable terminal 60 using, for example, a communication method based on the communication standard of BLE (Bluetooth Low Energy) or Wi-Fi (Wireless Fidelity).

Figure 5:
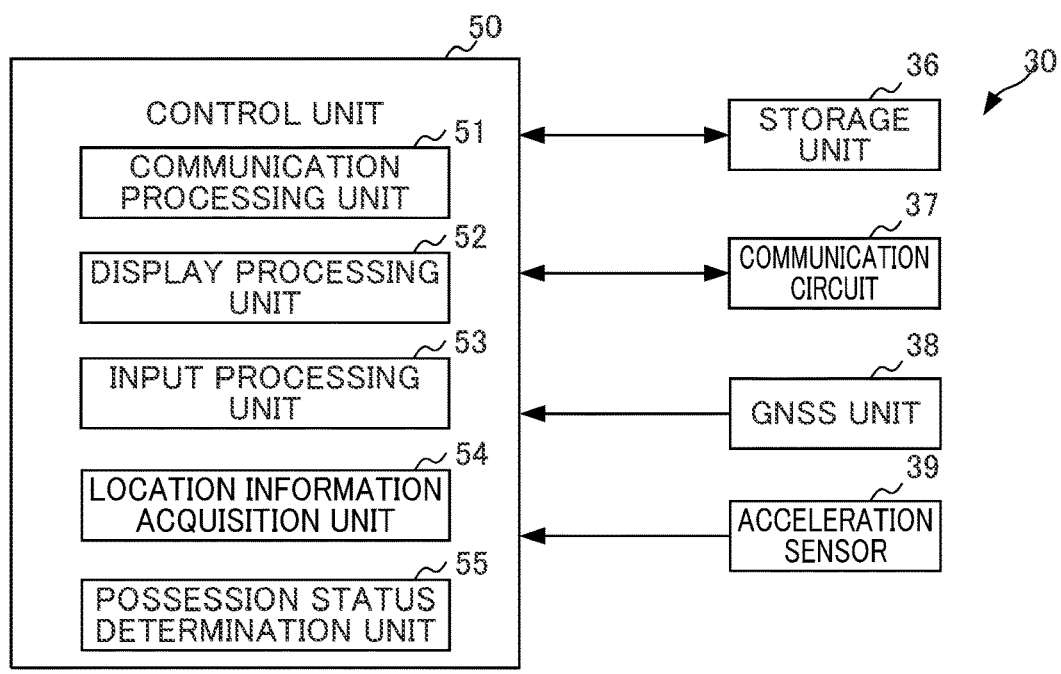
FIG. 5 is a functional block diagram illustrating a part of the functional configuration of a deliverer terminal according to an embodiment of the present invention.

Next, the functional configuration of the deliverer terminal 30 will be described. FIG. 5 is a functional block diagram illustrating a part of the functional configuration of the deliverer terminal 30 according to an embodiment of the present invention.

The control unit 50, which manages various controls of the deliverer terminal 30, is implemented by the CPU 31 that executes computation processing. The control unit 50 in the present embodiment performs as a communication processing unit (communication processing function) 51, a display processing unit (display processing function) 52, an input processing unit (input processing function) 53, a location information acquisition unit (location information acquisition function) 54, and a possession status determination unit (possession status determination function) 55.

The CPU 31 as communication processing unit 51 executes processing for exchanging various types of information with the delivery management server 10 via the communication unit 37, and executes processing for exchanging various types of information with the wearable terminal 60 via the short-range communication unit 45.

The CPU 31 as display processing unit 52 executes processing for displaying images on the output unit 35 of the deliverer terminal 30. For example, the display processing unit 52 executes processing for displaying delivery-related information on the deliverer terminal 30, based on the information acquired from the delivery management server 10.

The CPU 31 as input processing unit 53 executes processing for receiving operations of the input unit 34 by the user (deliverer). For example, the input processing unit 53 executes processing for receiving an operation indicating that the deliverer has accepted the delivery, based on the information displayed on the output unit 35.

The CPU 31 as location information acquisition unit 54 executes processing for acquiring the first location information that indicates the current location of the deliverer terminal 30, based on the positioning signal detected by the GNSS unit 38.

The CPU 31 as possession status determination unit 55 acquires possession status information indicating whether the deliverer actually possesses the deliverer terminal 30. Note that the term "possession status" herein does not necessarily mean that the deliverer as a user is actually holding the deliverer terminal 30 in their hand, or has the deliverer terminal 30 in a pocket of their clothes. For example, the term "possession status" also includes situations where the deliverer terminal 30 is put in a bag possessed by the deliverer, the deliverer terminal 430 is attached to a transportation option such as a bicycle, motorcycle, or car used by the deliverer for delivery, or the deliverer terminal 30 is placed inside such transportation options. The state where the deliverer terminal 30 moves with the moving user or the deliverer terminal 30 is in a location communicable with the wearable terminal 60 by short-range wireless communication can also be referred to as a possession status. The processing for acquiring possession status information by the possession status determination unit 55 will be described later.

<Electronic Device>

Figure 6:
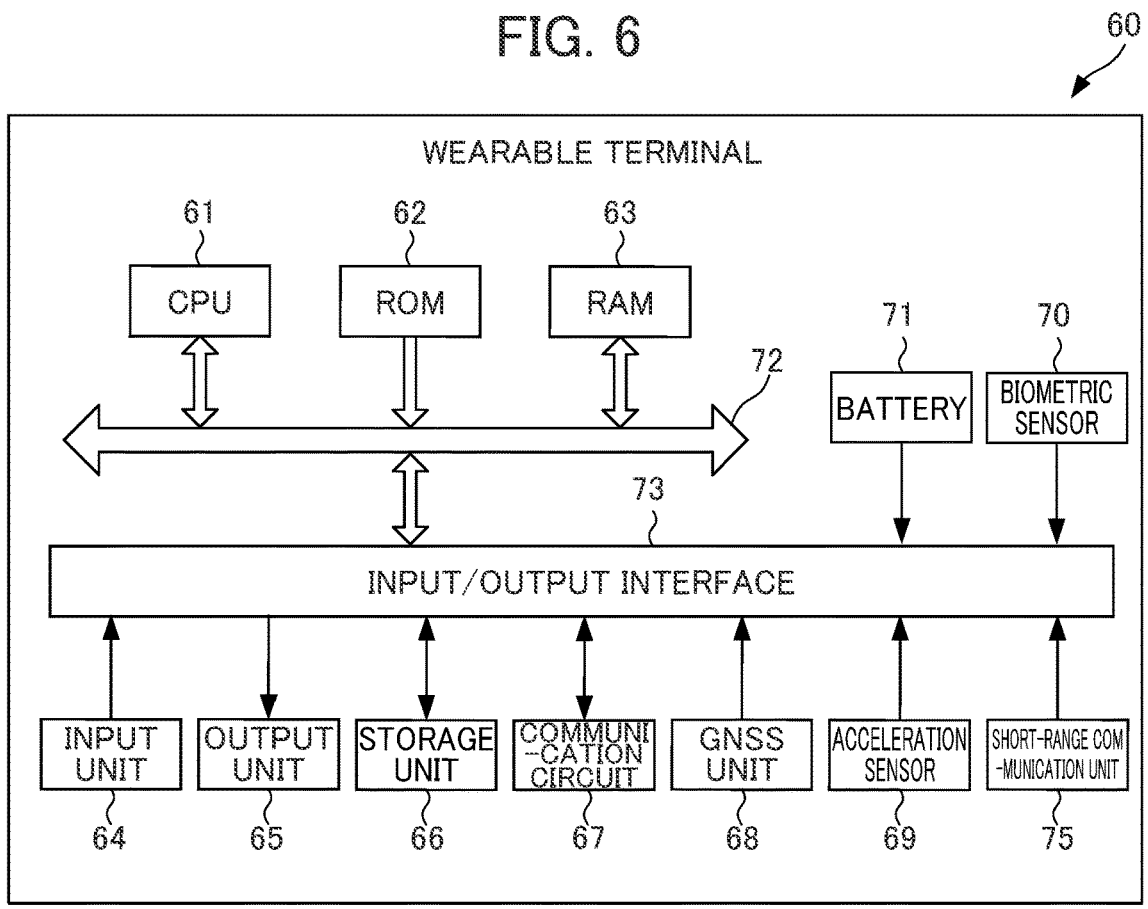
FIG. 6 is a block diagram illustrating a hardware configuration of a wearable terminal according to an embodiment of the present invention.

Next, an example of the wearable terminal 60 will be described. FIG. 6 is a block diagram illustrating the hardware configuration of the wearable terminal 60 according to an embodiment of the present invention.

The wearable terminal 60 of the present embodiment is a computer provided with a CPU 61, a ROM 62, a RAM 63, an input unit 64, an output unit 65, a storage unit 66, a communication circuit 67, a GNSS unit 68, an acceleration sensor 69, a biometric sensor 70, a battery 71, a bus 72, an input/output interface 73, and a short-range communication unit 75. Note that the same names may be assigned to common or similar configurations already described, and the detailed description thereof may be omitted.

The biometric sensor 70, which is not provided in the deliverer terminal 30, will be described. The biometric sensor 70 is a biometric information acquisition device that acquires biometric information on the user. The biometric information includes the user's heart rate and whether the wearable terminal 60 is in contact with the user's skin.

In the present embodiment, the biometric sensor 70 is positioned on the backside (the side in contact with the user) of the wearable terminal 60. An optical type or current detection type of biometric sensor based on electric current is used for the biometric sensor 70. In the case of the optical type, the biometric sensor 70 detects the user's biometric information by irradiating the user's skin with light and measuring the reflected light. In the case of the current detection type, the biometric sensor 70 acquires biometric information either by directly detecting a weak electric current on the user's skin, or by using a biometric impedance method, which involves applying a weak current to the skin to measure heart rate.

Figure 7:
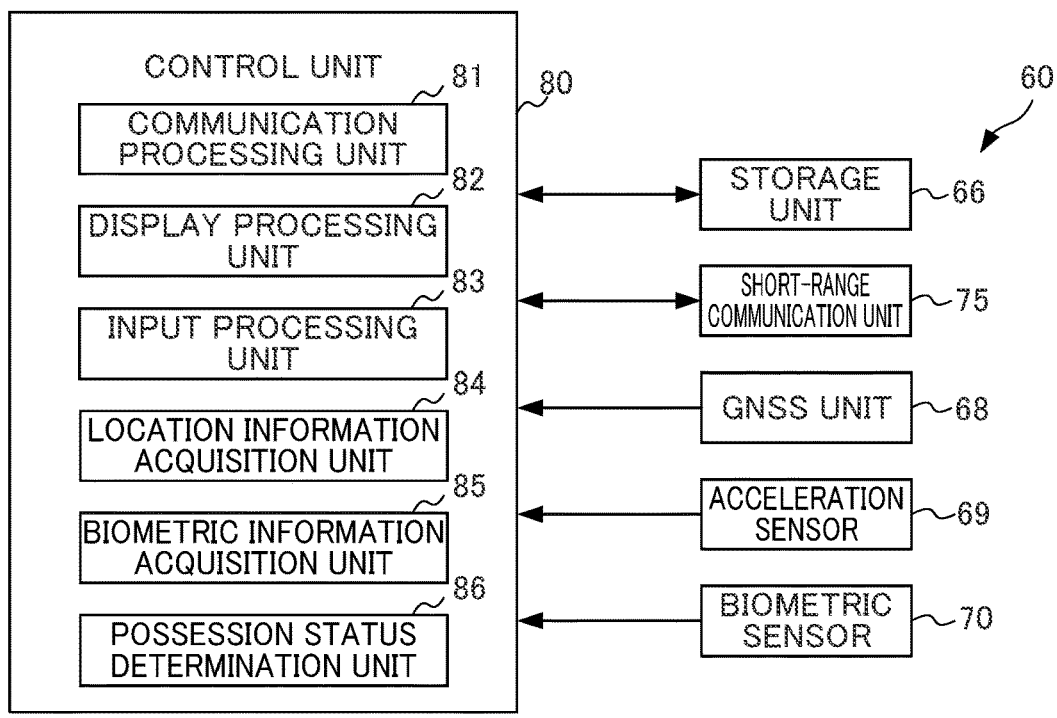
FIG. 7 is a functional block diagram illustrating a part of a functional configuration of the wearable terminal according to an embodiment of the present invention.

Next, the functional configuration of the wearable terminal 60 will be described. FIG. 7 is a functional block diagram illustrating a part of the functional configuration of the wearable terminal 60 in an embodiment of the present invention.

The control unit 80, which manages various controls of the wearable terminal 60, is implemented by the CPU 61 that executes computation processing. In the present embodiment, the control unit 80 performs as a communication processing unit (communication processing function) 81, a display processing unit (display processing function) 82, an input processing unit (input processing function) 83, a location information acquisition unit (location information acquisition function) 84, a biometric information acquisition unit (biometric information acquisition function) 85, and a possession status determination unit (possession status determination function) 86.

The CPU 61 as communication processing unit 81 executes processing of exchanging various information with the delivery management server 10 via the communication circuit 67, and executes processing of exchanging various information with the deliverer terminal 30 via the short-range communication unit 75.

The CPU 61 as display processing unit 82 executes processing of displaying images on the output unit 65 of the wearable terminal 60. For example, the display processing unit 82 executes processing of displaying the information acquired from the deliverer terminal 30 or the information acquired by the biometric information acquisition unit 85 to be described later.

The CPU 61 as input processing unit 83 executes processing of receiving operations of the input unit 64 by the user (deliverer). For example, the input processing unit 83 executes processing such as switching the information to be displayed, based on the information displayed on the output unit 65.

The CPU 61 as location information acquisition unit 84 executes processing of acquiring the second location information indicating the current location of the wearable terminal 60, based on the positioning signal detected by the GNSS unit 68.

The CPU 61 as biometric information acquisition unit 85 acquires biometric information such as information indicating the user's heart rate and whether the user is wearing the wearable terminal 60, based on the signal acquired from the biometric sensor 70.

The CPU 61 as possession status determination unit 86 executes processing of determining whether the deliverer actually possesses the deliverer terminal 30. This processing will be described later.

<Example of Delivery Processing>

Figure 8:
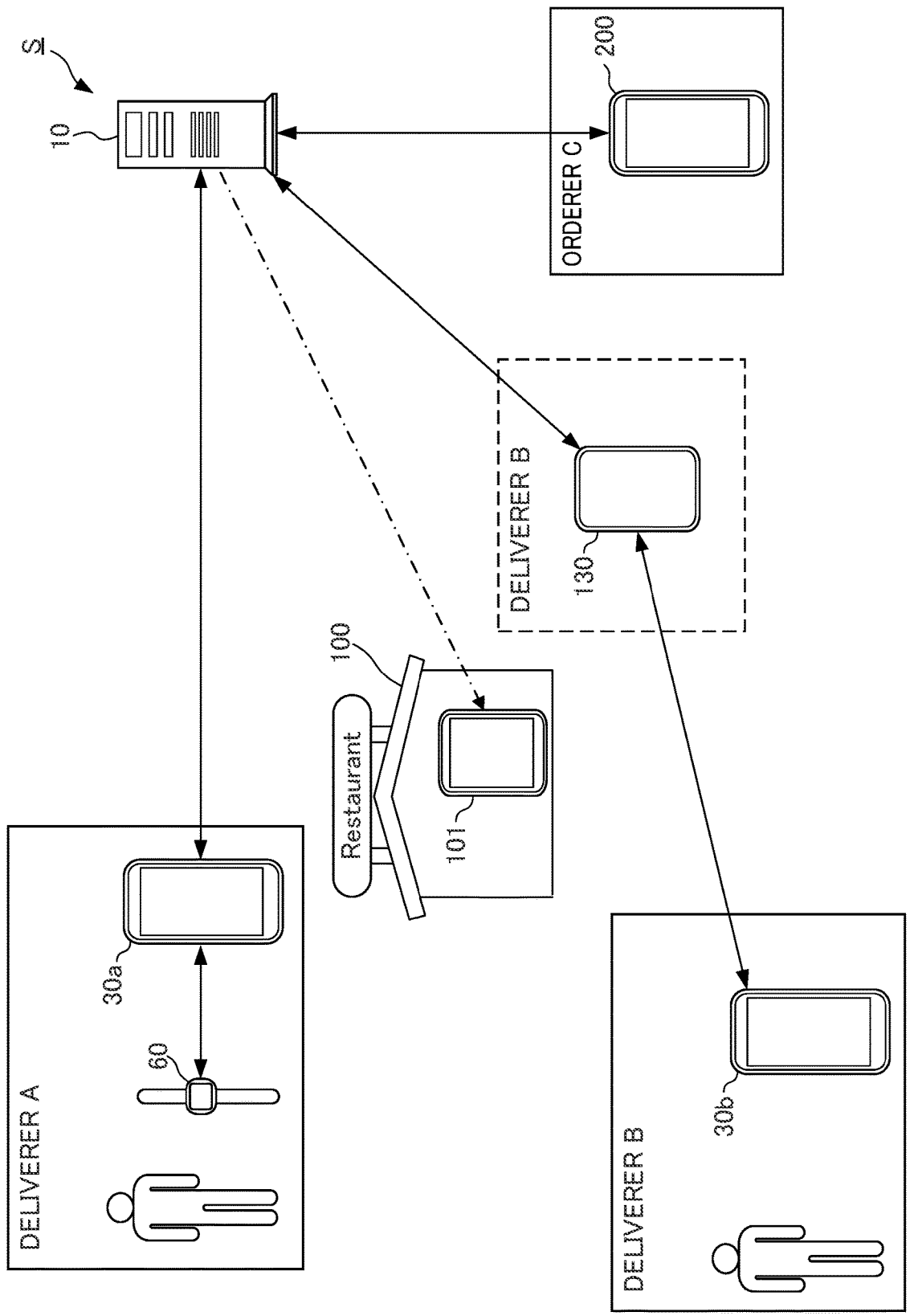
FIG. 8 is a schematic diagram illustrating delivery processing by the delivery management server, the deliverer terminal, and the wearable terminal according to an embodiment of the present invention.

Next, an example of delivery processing will be described. FIG. 8 is a schematic diagram illustrating the delivery processing by the delivery management server 10, the deliverer terminal 30, and the wearable terminal 60 according to an embodiment of the present invention. In the following description, the deliverer terminal 30 possessed by a deliverer A is referred to as a deliverer terminal 30a, and the deliverer terminal 30 possessed by a deliverer B is referred to as a deliverer terminal 30b.

As illustrated in FIG. 8, the deliverer A actually possesses the deliverer terminal 30a and the wearable terminal 60. On the other hand, the deliverer B actually possesses the deliverer terminal 30b, and has fixed a relay terminal 130 near the store 100 in an attempt to spoof the current location. This relay terminal 130 is a computer with the function of acquiring current location information and the function of responding to a request for location information from the delivery management server 10 with the location information of the relay terminal 130.

When the communication processing unit 21 of the delivery management server 10 receives order information from the orderer terminal 200 of an orderer C to the delivery management server 10, in which the order information requests delivery of a product of the store 100 to the home of the orderer C, the communication processing unit 21 starts delivery processing.

Figure 9:
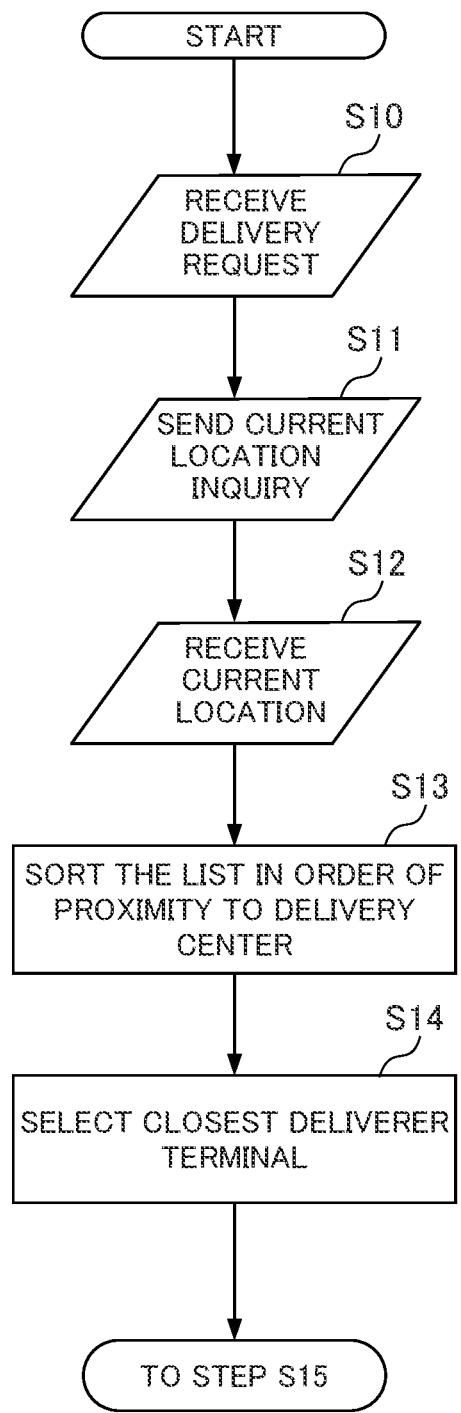
FIG. 9 is a first half of a flowchart illustrating an example of a flow of delivery processing by the delivery management server according to an embodiment of the present invention.
Figure 10:
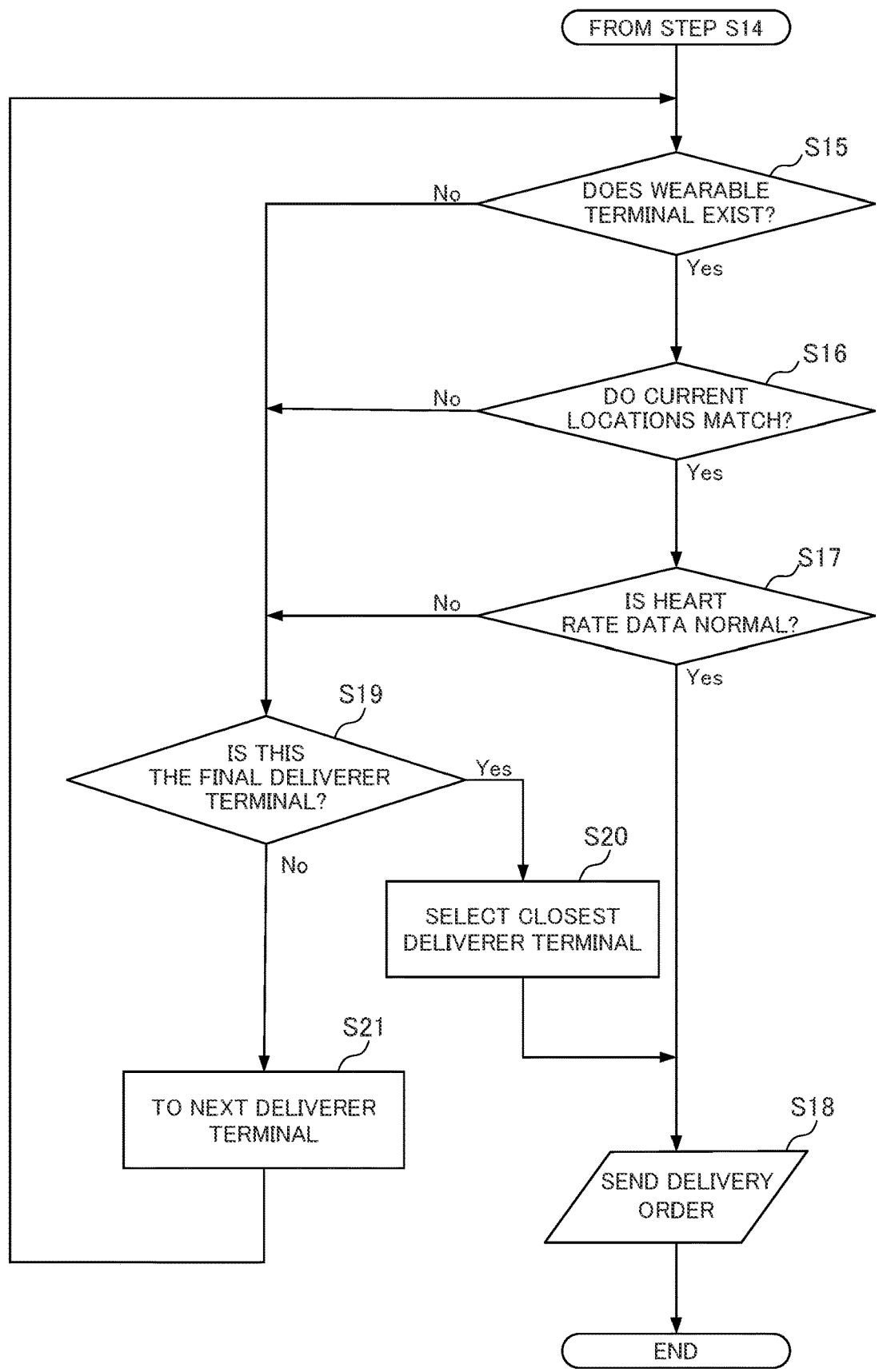
FIG. 10 is a latter half of the flowchart illustrating the example of the flow of delivery processing by the delivery management server according to an embodiment of the present invention.

Referring to FIGS. 9 and 10, the delivery processing of the delivery management server 10 is described. FIG. 9 is a flowchart of an example of the flow of the delivery processing by the delivery management server 10 according to an embodiment of the present invention, and FIG. 10 is the latter half of the flowchart.

As illustrated in FIG. 9, when the order processing unit 22 of the delivery management server 10 receives information indicating a delivery request from the delivery management server 10 (Step S10), the deliverer selection unit 23 sends information for inquiring the current location to the plurality of deliverer terminals 30 (Step S11). The plurality of deliverer terminals 30 are registered in the deliverer database 26, and include the deliverer terminals 30a and 30b.

When the deliverer selection unit 23 acquires the current location information from each of the plurality of deliverer terminals (Step S12), the deliverer selection unit 23 sorts the list of candidate deliverer terminals 30, based on each of the current location information (Step S13). In this sorting processing, the closer to the store 100, the higher the ranking in the list.

Next, the deliverer selection unit 23 selects the closest deliverer terminal 30 (Step S14). In the example of FIG. 8, although the deliverer terminal 30b is located further away from the store 100 than the deliverer terminal 30a, because the relay terminal 130 is located closer to the store 100 than the deliverer terminal 30a, at this point the deliverer terminal 30b is ranked higher than the deliverer terminal 30a.

Next, the deliverer selection unit 23 determines whether the deliverers possess a wearable terminal 60 along with the deliverer terminal 30 (Step S15 in FIG. 10). In the example in FIG. 8, since the relay terminal 130 of the deliverer B is not paired with the wearable terminal 60, it is determined that the deliverer B does not possess a wearable terminal 60. On the other hand, since the deliverer terminal 30a of the deliverer A is paired with a wearable terminal 60 (Step S15: Yes), it is determined that the deliverer A possesses the wearable terminal 60.

In the case where the wearable terminal 60 is possessed, the deliverer selection unit 23 determines whether the current location of the deliverer terminal 30 and the current location of the wearable terminal 60 match (Step S16). The term "match" herein includes not only the cases of complete match, but also the cases where the current location of the deliverer terminal 30 and the current location of the wearable terminal 60 are considered to be at the same place. In the example of FIG. 8, since the deliverer A actually possesses both the deliverer terminal 30a and the wearable terminal 60, the first location information of the deliverer terminal 30a and the second location information of the wearable terminal 60 match (Step S16: Yes).

In the case where the first location information of the deliverer terminal 30a and the second location information of the wearable terminal 60 match, the deliverer selection unit 23 determines whether the heart rate data acquired by the wearable terminal 60 is normal (Step S17). If the heart rate data is normal, the deliverer selection unit 23 sends delivery order information, which requests delivery, to the deliverer terminal 30 (Step S18).

Next, description is provided on the case where any one of the determination processing in Steps S15, S16, and S17 is determined to be 'No'. If any one of the determination processing in Steps S15, S16, and S17 was 'No', the processing advances to Step S19 (Step S15: No; Step S16: No; Step S17: No).

In Step S19, the deliverer selection unit 23 determines whether the deliverer terminal 30, which has undergone the determination of 'No' in Steps S15 through S17, is the final deliverer terminal 30. The final deliverer terminal 30 herein refers to the deliverer terminal 30 at the bottom of the list, based on the current location.

If this is not the final deliverer terminal 30, a deliverer terminal 30 as the next most promising candidate is selected from the list (Step S21). The deliverer selection unit 23 returns the processing to Step S15, and the determination processing of Step S15 is executed for the newly selected deliverer terminal 30. In the example of FIG. 8, after the deliverer terminal 30b, the determinations in Steps S15 through S17 are made on the deliverer terminal 30a. If the determinations on the deliverer terminal 30a are all 'Yes' in Steps S15 through S17, the deliverer terminal 30a will receive the delivery order.

In Step S19, if the deliverer terminal 30 is final, there would be no object left for the determination processing, so the deliverer selection unit 23 advances the processing to Step S20 (Step S19: Yes). Then, the deliverer selection unit 23 selects the deliverer terminal 30 that is closest to the store 100 (Step S20), and places a delivery order to the selected deliverer terminal 30 (Step S18). In this case, all of the plurality of deliverer terminals 30 have undergone the determination of 'No' in Steps S15 through S17, and a deliverer terminal 30 for placing a delivery order will be selected solely based on the current location.

Figure 11:
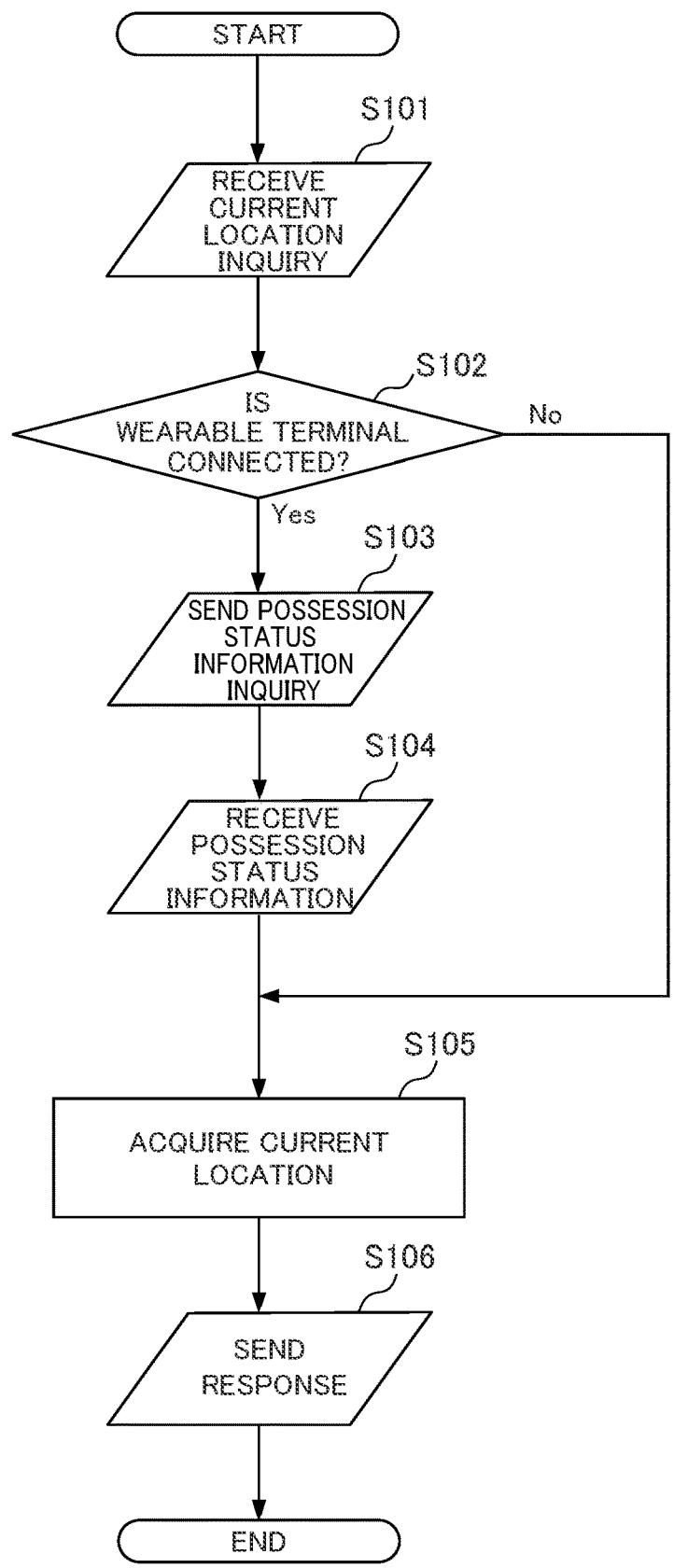
FIG. 11 is a flowchart illustrating an example of a flow of delivery processing by the deliverer terminal according to an embodiment of the present invention.

Next, the processing on the side of the deliverer terminal 30a possessed by the deliverer A will be described. FIG. 11 is a flowchart illustrating an example of the flow of the delivery processing by the deliverer terminal 30a according to an embodiment of the present invention.

When the communication processing unit 51 of the deliverer terminal 30a receives information indicating a current location inquiry from the delivery management server 10 (Step S101), the possession status determination unit 55 checks the connection status of the wearable terminal 60 (Step S102). For example, the possession status determination unit 55 determines whether there is a wearable terminal 60 that can communicate via BLE.

When the possession status determination unit 55 confirms that the wearable terminal 60 is communicable (Step S102: Yes), the possession status determination unit 55 requests the wearable terminal 60 for the second location information indicating the current location and the possession status information indicating the possession status (Step S103).

The possession status determination unit 55 receives the second location information and the possession status information from the wearable terminal 60 (Step S104). For example, the possession status information may be biometric information acquired by the wearable terminal 60, or may be a result of determination by the wearable terminal 60, based on biometric information such as heart rate. Note that the biometric information includes not only data indicating that heart rate data was normally measured, but also data indicating that biometric information could not be acquired.

Next, the location information acquisition unit 54 acquires the first location information indicating the current location of the device itself, which is generated based on the positioning signal received by the GNSS unit 38 (Step S105). Then, the possession status determination unit 55 sends the possession status information as a response to the delivery management server 10 (Step S106). For example, the possession status information that is sent to the delivery management server 10 is a result of determination by the possession status determination unit 55, based on the first location information, the second location information, and the biometric information. Alternatively, the first location information, the second location information, and the biometric information may be sent to the delivery management server 10 as possession status information, and the delivery management server 10 may determine the possession status.

Figure 12:
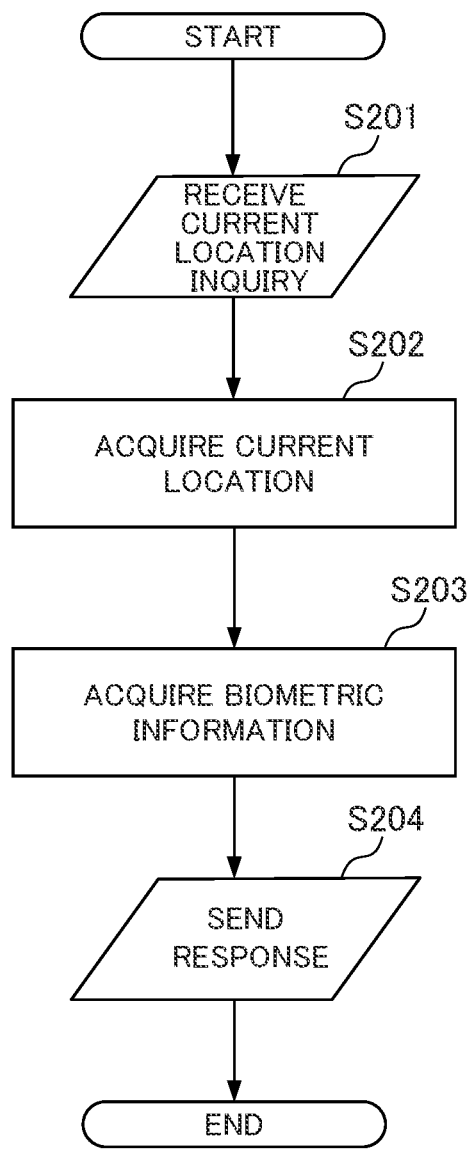
FIG. 12 is a flowchart illustrating an example of a flow of delivery processing by the wearable terminal according to an embodiment of the present invention.

Next, description is provided on the processing on the side of the wearable terminal 60 that is possessed by the deliverer A and communicates with the deliverer terminal 30a. FIG. 12 is a flowchart illustrating an example of the flow of delivery processing by the wearable terminal 60 according to an embodiment of the present invention.

When the communication processing unit 81 of the wearable terminal 60 receives information indicating a current location inquiry from the deliverer terminal 30a (Step S201), the location information acquisition unit 84 acquires the second location information indicating the current location of the wearable terminal 60, which is generated based on the positioning signal received by the GNSS unit 68 (Step S202). Then, the biometric information acquisition unit 85 acquires biometric information based on the detection value of the biometric sensor 70 (Step 3203). For example, the biometric information is heart rate data, etc.

Next, the possession status determination unit 86 sends the possession status information based on the second location information and the biometric information as a response to the deliverer terminal 30a (Step S204). The processing of the possession status information on the side of the deliverer terminal 30a is as described above.

Figure 13:
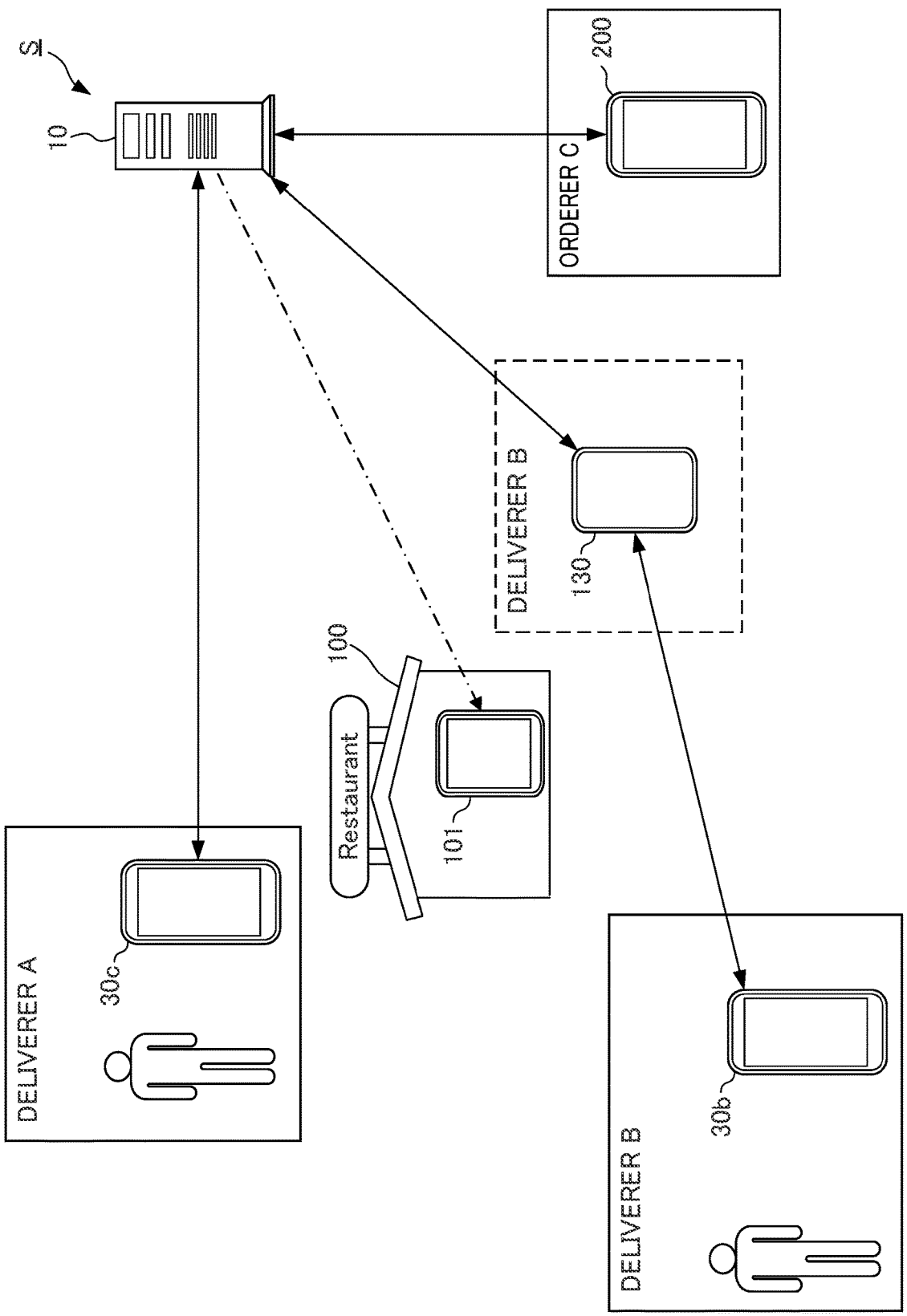
FIG. 13 is a schematic diagram illustrating delivery processing by the delivery management server and the deliverer terminal according to an embodiment of the present invention.

In the foregoing, the example of the deliverer A who possesses the wearable terminal 60 has been described. Next, an embodiment different from the above embodiment will be described. FIG. 13 is a schematic diagram illustrating delivery processing by the delivery management server 10 and a deliverer terminal 30c according to an embodiment of the present invention. Note that the same names or symbols are assigned to common or similar configurations already described, and the detailed description thereof is omitted.

In the embodiment of FIG. 13, the difference from the example of FIG. 8 is that the deliverer A does not possess the wearable terminal 60. In this example, the deliverer terminal 30c possessed by the deliverer A detects body motion of the deliverer A by the acceleration sensor 39 and determines whether the deliverer A actually possesses the deliverer terminal 30c, based on the body motion of the deliverer A. In other words, the deliverer terminal 30c alone determines the possession status.

Figure 14:
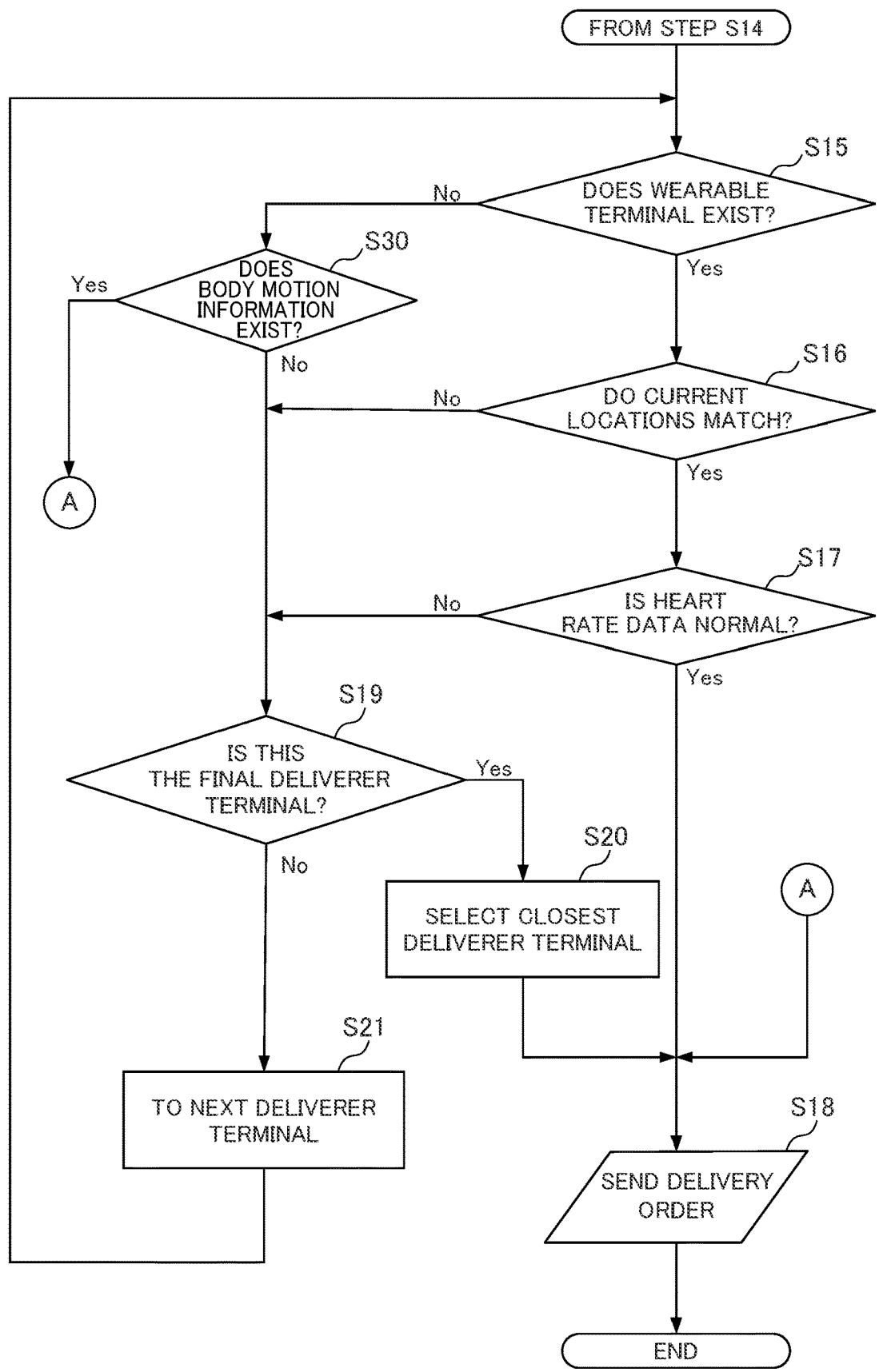
FIG. 14 is a latter half of the flowchart illustrating the example of the flow of delivery processing by the delivery management server according to an embodiment of the present invention.

Next, the processing on the side of the delivery management server 10 will be described with reference to FIG. 14. FIG. 14 is the latter half of the flowchart illustrating the example of the flow of delivery processing by the delivery management server according to an embodiment of the present invention. The flowchart of FIG. 14 is basically the same as the flowchart of FIG. 10. The difference from the flowchart of FIG. 10 is that the processing of Step S30 is added in the case of determining that there is no wearable terminal 60 in Step S15 (Step S15: No).

In Step S30, the deliverer selection unit 23 determines whether body motion information was included in the information sent from the deliverer terminal 30c (Step S30). If the body motion information was included (Step S30: Yes), it can be considered that the user possesses the deliverer terminal 30c, so the deliverer selection unit 23 advances the processing to the processing of placing a delivery order in Step S18. If the body motion information was not included (Step S30: No), the deliverer selection unit 23 advances the processing to Step S19. The processing after Step S19 is as described above.

Figure 15:
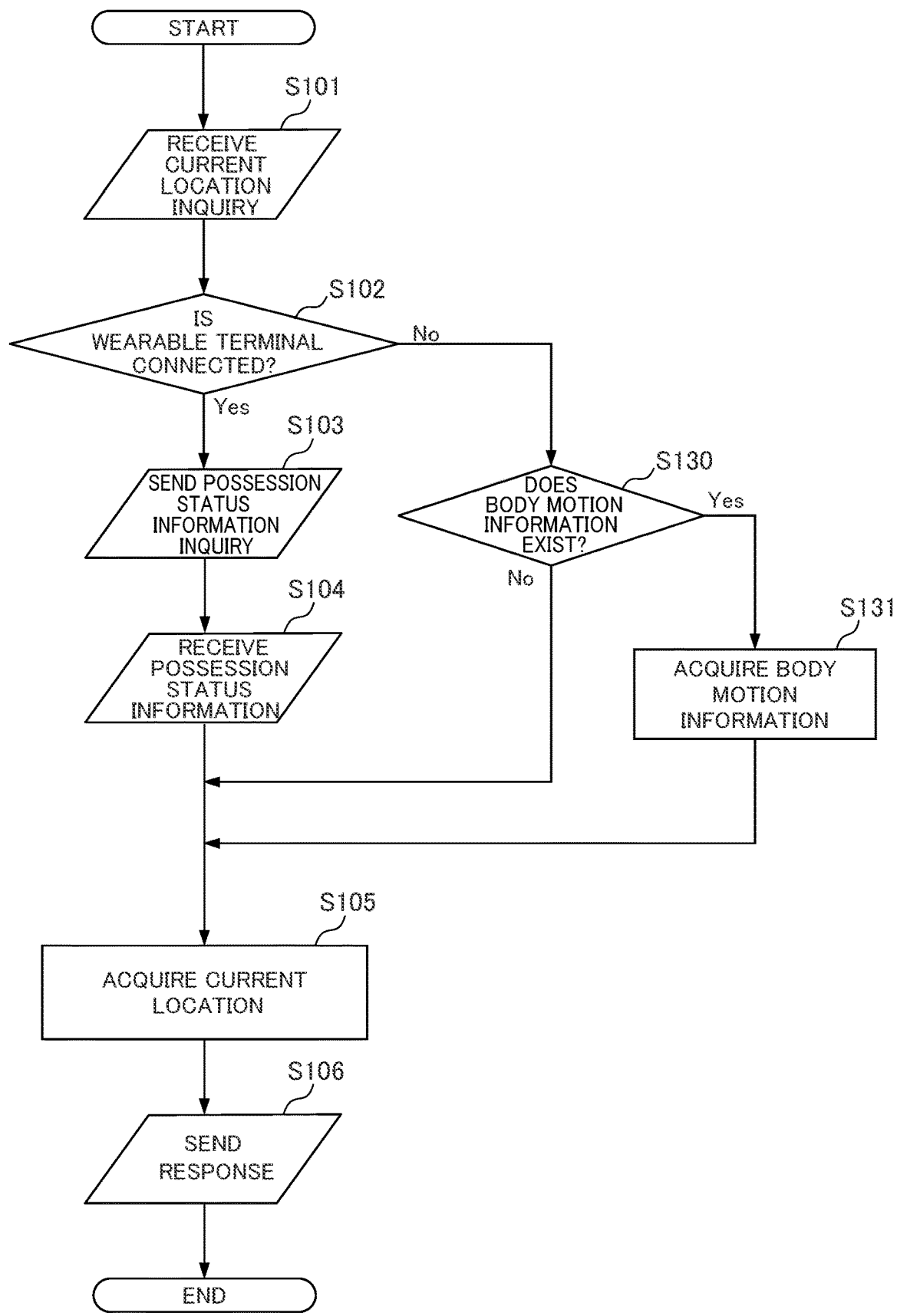
FIG. 15 is a flowchart illustrating an example of a flow of delivery processing by the deliverer terminal according to an embodiment of the present invention.

Next, referring to FIG. 15, the processing on the side of the deliverer terminal 30c will be described. FIG. 15 is a flowchart illustrating an example of the delivery processing by the deliverer terminal 30c according to an embodiment of the present invention. The flowchart of FIG. 15 is basically the same as the flowchart of FIG. 11. The processing in Steps S130 and S131 is added in the case of determining that there is no connection with the wearable terminal 60 in Step S102 (Step S102: No), which is the difference from the flowchart of FIG. 11.

In Step S130, the possession status determination unit 55 determines whether there is body motion information (Step S130). For example, the possession status determination unit 55 checks the most recent acceleration acquired by the acceleration sensor 39, and if the acceleration has been detected up to the most recent time, it is determined that the deliverer A is carrying the deliverer terminal 30c.

If there is body motion information in Step S130 (Step S130: Yes), the possession status determination unit 55 sets the possession status information, based on the body motion information (Step S131). Next, the possession status determination unit 55 advances the processing to Step S115 to acquire the first location information. Then, the possession status determination unit 55 executes the processing in Step S116 to send the body motion information along with the first location information to the delivery management server 10.

As described above, the delivery system S of the present embodiment includes: the deliverer terminal 30 and the delivery management server 10, the deliverer terminal 30, comprising: the communication unit 37 that communicates with the delivery management server 10; and one or more processors that performs the followings: acquiring the first location information indicating the current location of the device itself; acquiring biometric information on the deliverer (user) or body motion information on the deliverer (user); and acquiring possession status information indicating whether the device itself is possessed by the user, based on the acquired biometric information or the acquired body motion information, controlling the communication unit 37 to send the possession status information along with the first location information to the delivery management server 10, and the delivery management server 10 comprising: a communication circuit 17 that communicates with the deliverer terminal 30; and one or more processors that performs the following: acquiring the possession status information and the first location information from the deliverer terminal 30; determining whether a delivery order is to be placed, based on the acquired first location information and the acquired possession status information.

As a result, the possession status information allows for determination on whether the deliverer actually possesses a deliverer terminal; thus, spoofing by fixing the relay terminal 130 near the store 100 can be detected by the delivery management server 10. Therefore, the delivery management server 10 can select a deliverer A who is actually near the store 100.

In the present embodiment, the delivery system S further comprises the acceleration sensor 39 that acquires body motion information, and the one or more processors of the deliverer terminal 30 acquires the possession status by the user, based on the detection value of the acceleration sensor 39.

By using the detection value of the acceleration sensor 39, it can be determined whether the deliverer terminal 30c has been moving up to the most recent time; therefore, spoofing by fixing the relay terminal 130 near the store 100 can be detected by the processing of the deliverer terminal 30 alone.

In the present embodiment, the delivery system S further comprises the short-range communication unit 45 communicating with the wearable terminal 60 worn by the user and acquiring biometric information or body motion information, and the one or more processors of deliverer terminal 30 acquires the possession status of the user, based on the biometric information or the body motion information received from the wearable terminal 60 by the short-range communication unit 45.

This allows for a more accurate determination on the possession status of the user by utilizing the wearable terminal 60 worn by the user.

In the present embodiment, the one or more processors of the deliverer terminal 30 acquires the possession status of the user, based on the result of comparing the second location information received from the wearable terminal 60 by the short-range communication unit 45 and the first location information.

If the wearable terminal 60 worn on the body is at the same location as, or a location close to, the deliverer terminal 30, it is highly probable that the user actually possesses the deliverer terminal 30, so this method can also accurately determine the possession status of the user.

The wearable terminal 60 of the present embodiment includes: the short-range communication unit 75 that establishes communication with other deliverer terminals 30; the biometric sensor 70 that acquires biometric information on the user; the acceleration sensor 69 that acquires body motion information; and the control unit 80 that determines whether the wearable terminal 60 is possessed by the user, based on the biometric information or the body motion information. The control unit 80 controls the short-range communication unit 75 to send the possession status information on the possession status of the user, as determined by the control unit 80, to another deliverer terminal 30 via.

This allows for a more accurate determination on the possession status of the user by utilizing the wearable terminal 60 worn by the user.

The delivery management server 10 of the present embodiment includes: the communication circuit 17 that communicates with the deliverer terminal 30; and the control unit 20 that acquires the possession status information on the possession status of the deliverer terminal 30 or the wearable terminal 60 worn by the user, based on the information received by the communication circuit 17. The control unit 20 determines whether a delivery order should be placed, based on the first location information indicating the current location of the deliverer terminal 30, as received from the deliverer terminal 30 by the communication circuit 17, and the possession status information.

This allows for determination on whether the deliverer actually possesses the deliverer terminal 30, based on the possession status information; thus, spoofing by fixing the relay terminal 130 near the store 100 can be detected by the delivery management server 10. Therefore, the delivery management server 10 can select a deliverer A who is actually near the store 100.

The one or more processors of the delivery management server 10 preferentially sets the deliverer terminal 30a, which sent the possession status information indicating that the user possesses a deliverer terminal, as the target for delivery order, rather than the deliverer terminal 30b which sent the possession status information indicating that the user does not possess a deliverer terminal.

This allows for a more reliable selection of a deliverer who is near the store 100.

An embodiment and variations of the present invention have been described above. The present invention is not limited to the embodiment and variations. It is also acceptable to combine each of the embodiment and variations, and modifications and improvements within the range that can achieve the purpose of the present invention are included in the present invention.

In the aforementioned embodiment, a configuration has been described in which the deliverer terminal 30 acquires possession status information by utilizing the wearable terminal 60, in the food delivery services such as restaurants; however, the present invention is not limited to this configuration. For example, an acceleration sensor may be placed in a deliverer's bag or delivery bag for holding products, and the deliverer terminal 30 may acquire possession status information, based on the detected value of the acceleration sensor. A motion monitoring sensor for monitoring operations of the pedal of the bicycle used by the deliverer may be installed, and the deliverer terminal 30 may acquire possession status information, based on the detected value of the movement monitoring sensor. A drive monitoring sensor for monitoring operations of the drive source (such as a motor or engine) of a four-wheeled or two-wheeled vehicle used by the deliverer may be installed, and the deliverer terminal 30 may acquire possession status information, based on the detected value of the drive monitoring sensor.

The processing of each step described with reference to the flowchart may partly be omitted, or add steps as appropriate, or combine some conditions. For example, the possession status may be determined by acquiring both biometric information and motion information.

The functional configuration in the present embodiment is implemented by a processor executing computation processing, and the processors that can be used in the present embodiment include not only those composed of various processing devices such as a single processor, a multiprocessor, and a multicore processor, but also include those combined with processing circuits such as ASIC (Application Specific Integrated Circuit) and FPGA (Field-Programmable Gate Array).

The series of processing mentioned above can be executed either by hardware or software. In other words, the functional configurations illustrated in the above embodiment and variations are merely examples and are not limited in particular. That is, as long as the functions that can execute the above-mentioned series of processing as a whole are provided, whatever functional blocks used for achieving these functions are not limited in particular to the above embodiment and variations. One functional block may be composed of only hardware, only software, or a combination of them.

When executing the series of processing by software, the program that composes the software is installed from a network or a recording medium to a computer. The computer may be a dedicated computer built into hardware. The computer may be a general-purpose personal computer, capable of executing various functions by installing various programs.

The recording medium that contains the program may be distributed separately from the device itself to provide the program to users, or may be a recording medium provided to users in a state of being pre-installed in the device body. The steps describing the program recorded on the recording medium includes not only processing sequentially executed in accordance with the order but also processing that are not necessarily sequentially executed and are executed in parallel or individually.

The hardware configuration illustrated in the above embodiment and variations is merely an example and is not limited in particular to this configuration. In addition to those composed of various processing devices such as single processors, multiprocessors, and multicore processors, those combined with processing circuits such as ASIC (Application Specific Integrated Circuit) and FPGA (Field-Programmable Gate Array) may be adopted to implement the functional configuration as a processor.

This application is based on Japanese Patent Application No. 2021-025367 filed on Feb. 19, 2021. The specification, claims, and entire drawings of Japanese Patent Application No. 2021-025367 are incorporated herein by reference.

INDUSTRIAL APPLICABILITY

The present invention can appropriately determine whether a deliverer is near the store where the product will be received.

EXPLANATION OF REFERENCE NUMERALS

10: delivery management server
17: communication circuit
20: control unit (processor)
30: deliverer terminal
37: communication circuit
38: GNSS unit
39: acceleration sensor
45: short-range communication unit
50: control unit (processor)
60: wearable terminal
67: communication circuit
68: GNSS unit
69: acceleration sensor
70: biometric sensor
75: short-range communication unit

The invention claimed is:
1. A system including:
a plurality of electronic devices and a server,
an electronic device of the plurality of electronic devices, comprising:
a first wireless communication circuit that communicates with the server; and
one or more processors that perform:
acquiring first location information acquired based on a positioning signal received from a first positioning unit included in the electronic device, and indicating a current location of the electronic device;
acquiring biometric information of a user acquired based on a detected value of a biometric sensor included in a wearable electronic device connected by short-range wireless communication with the electronic device and worn by the user, or body motion information of the user acquired based on a detected value of an acceleration sensor included in the electronic device;
acquiring possession status information indicating whether the electronic device is possessed by the user, based on the acquired biometric information or the acquired body motion information; and controlling the first wireless communication circuit to send the possession status information along with the first location information to the server, and the server, comprising:
a communication circuit that communicates with the electronic device; and
one or more processors that performs the following:
acquiring the possession status information and the first location information from the electronic device; and
determining whether a delivery order is to be placed, based on the acquired first location information and the acquired possession status information,
preferentially setting, from among the plurality of electronic devices, the electronic device which sent, as the possession status information, possession status information indicating that the user possesses the electronic device or the wearable electronic device, and the first location information, as a target for the delivery order, over a second electronic device from among the plurality of electronic devices, which sent only second location information indicating, as a second possession status information, that a second user does not possess the second electronic device or a second wearable device connected by short-range wireless communication with the second electronic device and worn by the second user.

2. The system according to claim 1,
wherein:
the electronic device further comprises a second wireless communication circuit that performs short-range wireless communication with the wearable electronic device, and
the one or more processors of the electronic device acquires the possession status information based on the body motion information or the biometric information received from the wearable electronic device via the second wireless communication circuit.

3. The system according to claim 1,
wherein the electronic device further comprises a second wireless communication circuit that performs short-range wireless communication with the wearable electronic device and acquires, from the wearable electronic device, second a wearable electronic device location information indicating a location of the wearable electronic device and which is acquired based on a positioning signal received from a second positioning unit included in the wearable electronic device,
wherein the one or more processors of the electronic device acquires the possession status information based further on a result of comparison between the first location information and the wearable electronic device location information received from the wearable electronic device via the second wireless communication circuit.

4. A non-transitory computer-readable storage medium storing a program that is executed by a computer that comprises a processor to control a system including: a plurality of electronic devices; an electronic device of the plurality of electronic devices including a first wireless communication circuit that communicates with a server; and the server including a communication circuit that communicates with the electronic device, the program being executable to cause the computer to perform operations comprising:
acquiring first location information acquired based on a positioning signal received from a first positioning unit included in the electronic device, and indicating a current location of the electronic device;
acquiring biometric information of a user acquired based on a detected value of a biometric sensor included in a wearable electronic device connected by short-range wireless communication with the electronic device and worn by the user, or body motion information of the user acquired based on a detected value of an acceleration sensor included in the electronic device;
acquiring possession status information indicating whether the electronic device is possessed by the user, based on the acquired biometric information or the acquired body motion information;
controlling the first wireless communication circuit to send the possession status information along with the first location information to the server, and acquiring the possession status information and the first location information from the electronic device; and
determining whether a delivery order is to be placed, based on the acquired first location information and the acquired possession status information,
preferentially setting, from among the plurality of electronic devices, the electronic device which sent, as the possession status information, possession status information indicating that the user possesses the electronic device or the wearable electronic device, and the first location information, as a target for the delivery order, over a second electronic device from among the plurality of electronic devices, which sent only second location information indicating, as a second possession status information, that a second user does not possess the second electronic device or a second wearable device connected by short-range wireless communication with the second electronic device and worn by the second user.

5. The non-transitory computer-readable storage medium according to claim 4,
wherein the electronic device further comprises a second wireless communication circuit that performs short-range wireless communication with the wearable electronic device,
wherein the program is executable to cause the computer to perform operations further comprising acquiring the possession status information based on the body motion information or the biometric information received from the wearable electronic device via the second wireless communication circuit.

6. The non-transitory computer-readable storage medium according to claim 4,
wherein the electronic device further comprises a second wireless communication circuit that performs short-range wireless communication with the wearable electronic device worn by the user and acquires, from the wearable electronic device, a wearable electronic device location information indicating a location of the wearable electronic device and which is acquired based on a positioning signal received from a second positioning unit included in the wearable electronic device,
wherein the program is executable to cause the computer to perform operations further comprising acquiring the possession status information, based further on a result of comparison between the first location information and the wearable electronic device location information received from the wearable electronic device via the second wireless communication circuit.

7. A method executed by a system to determine a possession status, the system including: a plurality of electronic devices; an electronic device of the plurality of electronic devices comprising a first wireless communication circuit that communicates with a server; and the server comprising a communication circuit that communicates with the electronic device, the method comprising:

acquiring first location information acquired based on a positioning signal received by a first positioning unit included in the electronic device, and indicating a current location of the electronic device;

acquiring biometric information acquired based on a detected value of a biometric sensor included in a wearable electronic device connected by short-range wireless communication with the electronic device and worn by a user, or body motion information of the user acquired based on a detected value of an acceleration sensor included in the electronic device;

acquiring possession status information indicating whether the electronic device is possessed by the user, based on the acquired biometric information or the acquired body motion information;

controlling the first wireless communication circuit to send the possession status information along with the first location information to the server;

acquiring the possession status information and the first location information from the electronic device; and determining whether a delivery order is to be placed, based on the acquired first location information and the acquired possession status information, preferentially setting, from among the plurality of electronic devices, the electronic device which sent, as the possession status information, possession status information indicating that the user possesses the electronic device or the wearable electronic device, and the first location information, as a target for the delivery order, over a second electronic device from among the plurality of electronic devices, which sent only second location information indicating, as a second possession status information, that a second user does not possess the second electronic device or a second wearable device connected by short-range wireless communication with the second electronic device and worn by the second user.

8. The method according to claim 7, wherein the electronic device of the system further comprises a second wireless communication circuit that performs short-range wireless communication with the wearable electronic device, and wherein the method further comprises acquiring the possession status information, based on the body motion information or the biometric information received from the wearable electronic device via the second wireless communication circuit.

9. The method according to claim 7, wherein the electronic device further comprises a second wireless communication circuit that performs short-range wireless communication with the wearable electronic device worn by the user and acquires, from the wearable electronic device, a wearable electronic device location information indicating a location of the wearable electronic device and which is acquired based on a positioning signal received by a second positioning unit included in the wearable electronic device, and wherein the method further comprises acquiring the possession status by the user, based further on a result of comparison between the first location information and the wearable electronic device location information received from the wearable electronic device via the second wireless communication circuit.

* * * * *

UNITED STATES PATENT AND TRADEMARK OFFICE
CERTIFICATE OF CORRECTION

PATENT NO. : 12,260,369 B2  
APPLICATION NO. : 18/229223  
DATED : March 25, 2025  
INVENTOR(S) : Fuminobu Nakamura Page 1 of 1

It is certified that error appears in the above-identified patent and that said Letters Patent is hereby corrected as shown below:

In the Claims

Column 15, Line 49 (Claim 3, Line 6), delete "second".

Signed and Sealed this  
Seventeenth Day of June, 2025

Coke Morgan Stewart  
*Acting Director of the United States Patent and Trademark Office*